US 6,547,955 B1

(12) United States Patent
Hada et al.

(10) Patent No.: US 6,547,955 B1
(45) Date of Patent: Apr. 15, 2003

(54) GAS CONCENTRATION MEASURING APPARATUS DESIGNED TO MINIMIZE ERROR COMPONENT CONTAINED IN OUTPUT

(75) Inventors: Satoshi Hada, Kariya (JP); Eiichi Kurokawa, Okazaki (JP); Tomoo Kawase, Nagoya (JP); Toshiyuki Suzuki, Handa (JP); Satoshi Haseda, Okazaki (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/453,518

(22) Filed: Dec. 3, 1999

(30) Foreign Application Priority Data

Dec. 4, 1998 (JP) .......................... 10-345654

(51) Int. Cl.[7] .......................................... G01N 27/407
(52) U.S. Cl. .................. 205/781; 205/784.5; 205/785; 205/787; 204/406; 204/424; 204/425
(58) Field of Search ................. 204/406, 425, 204/426; 205/781, 784.5, 787, 785

(56) References Cited

U.S. PATENT DOCUMENTS

| 4,457,808 A | * | 7/1984 | Taylor et al. ............... 204/401 |
| 4,796,587 A | * | 1/1989 | Nakajima et al. ............ 204/406 |
| 4,822,456 A | * | 4/1989 | Bryan ........................ 204/412 |
| 4,908,575 A | | 3/1990 | Usami et al. ............... 324/711 |
| 5,672,811 A | | 9/1997 | Kato et al. ................. 73/31.05 |
| 5,989,624 A | * | 11/1999 | Kida et al. .................. 427/125 |
| 6,084,418 A | * | 7/2000 | Takami et al. .............. 204/424 |
| 6,214,207 B1 | * | 4/2001 | Miyata et al. .............. 205/781 |
| 6,347,277 B2 | * | 2/2002 | Amtmann et al. .......... 204/406 |

FOREIGN PATENT DOCUMENTS

| EP | 120423 | 10/1984 |
| EP | 695983 | 2/1996 |
| EP | 849591 | 6/1998 |
| JP | 59-170723 | 9/1984 |
| JP | 3-91945 | 9/1991 |
| JP | 8-271476 | 10/1996 |
| JP | 10-232220 | 9/1998 |
| JP | 11-72478 | 3/1999 |
| WO | 98/13686 | 4/1998 |
| WO | 98/48266 | 10/1998 |

* cited by examiner

Primary Examiner—Robert J. Warden, Sr.
Assistant Examiner—Kaj K. Olsen
(74) Attorney, Agent, or Firm—Nixon & Vanderhye P.C.

(57) ABSTRACT

A gas concentration measuring apparatus which has a gas sensor designed to measure, for example, the concentrations of $O_2$ and HOx contained in exhaust emissions of an automotive engine is provided. The apparatus includes a signal processing circuit which converts a current signal outputted from the gas sensor as a function of the concentration of either of $O_2$ and HOx into a voltage signal. The gas sensor and the signal processing circuit are connected electrically through a conductor. The conductor has a length which is determined as a function of a level of the current signal outputted from the gas sensor. The weaker the level of the current signal is, the shorter the length of the conductor. This minimizes addition of electrical noises to the current signal outputted from the gas sensor.

6 Claims, 10 Drawing Sheets

GAS CONCENTRATION MEASURING APPARATUS DESIGNED TO MINIMIZE ERROR COMPONENT CONTAINED IN OUTPUT

BACKGROUND OF THE INVENTION

1. Technical Field of the Invention

The present invention relates generally to a gas concentration measuring apparatus for measuring the concentration of gases which may be employed in an air-fuel ratio control system for automotive vehicles, and more particularly to a gas concentration measuring apparatus designed to minimize an error component contained in an output thereof.

2. Background Art

Recently, NOx sensors designed to measure the concentration of nitrogen oxide (NOx) contained in exhaust emissions of automotive engines are proposed and put into practical use.

As one of such NOx sensors, a gas sensor is known which is designed to measure the concentrations of NOx and $O_2$ contained in exhaust gasses of the engine simultaneously. This type of gas sensor includes a pump cell for decomposing or ionizing oxygen molecules contained in exhaust gasses to measure the concentration of $O_2$ and a sensor cell for decomposing NOx in the oxygen-decomposed exhaust gasses to measure the concentration of NOx. The measurement of the concentration of each of NOx and $O_2$ is achieved by applying a given voltage to a corresponding one of the pump cell and the sensor cell to induce flow of current as a function of one of the concentrations of NOx and $O_2$. The current is outputted from the gas sensor and converted into a voltage signal which is, in turn, used in, for example, an engine control unit of the vehicle.

The above gas sensor, however, has the drawback in that the amount of current flowing through the cell sensor as a function of the concentration of NOx is extremely small, so that it apt to interfere with electrical noises, resulting in a failure in measuring the concentration of NOx accurately. Specifically, when the concentration of NOx is within 0 to 2000 ppm, a current output from the sensor cell is as little as 5 to 10 $\mu$A. Therefore, in the case where the gas sensor is used in an engine control system of an automotive vehicle, signal outputs from peripheral electrical devices are added to an output of the gas sensor as noises which will produce an error in measuring the concentration of NOx.

SUMMARY OF THE INVENTION

It is therefore a principal object of the present invention to avoid the disadvantages of the prior art.

It is another object of the present invention to provide a gas concentration measuring apparatus designed to minimize an error component contained in an output of the apparatus.

According to one aspect of the invention, there is provided a gas concentration measuring apparatus. The gas concentration measuring apparatus includes: (a) a gas concentration sensor outputting a signal as a function of concentration of a given component of gasses; (b) a signal processing circuit processing the signal outputted from the gas concentration sensor to produce a voltage signal indicative of the concentration of the given component of the gasses; and (c) a conductor electrically connecting the gas concentration sensor and the signal processing circuit for transmission of the signal. The conductor has a length which is determined as a function of a level of the signal outputted from the gas concentration sensor. The weaker the level of the signal is, the shorter the length of the conductor.

In the preferred mode of the invention, a connector is provided which connects the gas concentration sensor with an external device. The connector has disposed therein the signal processing circuit.

An impedance measuring circuit is provided which measures the impedance of a sensor element of the gas concentration sensor. The impedance measuring circuit is integrated in a single unit together with the signal processing circuit.

A heater and a heater control circuit are provided. The heater heats up a sensor element of the gas concentration sensor. The heater control circuit controls a power supply to the heater. The heater control circuit is integrated in a single unit together with the signal processing circuit.

The gas concentration measuring apparatus may be mounted in a vehicle to measure, for example, the concentrations of $O_2$ and NOx contained in exhaust emissions of a combustion engine for use in an air-fuel ratio control. The weaker the level of the signal is, the shorter a distance between the gas concentration sensor and the signal processing circuit for minimizing addition of electrical noises produced by electrical devices mounted in the vehicle to the signal outputted from the gas concentration sensor.

The gas concentration sensor includes a first cell responsive to application of a voltage to discharge oxygen contained in the gasses outside the gas concentration sensor, producing a first electric current as a function of concentration of the discharged oxygen and a second cell responsive to application of a voltage to produce a second electric current as a function of concentration of a specified gas component contained in the gasses from which the oxygen is discharged by the first cell.

The signal processing circuit has a function of compensating for a unit-to-unit variation in characteristic of the gas concentration sensor.

The signal processing circuit corrects an output characteristic of the gas concentration sensor so as to agree with a desired one.

The impedance measuring circuit has a function of compensating for a unit-to-unit variation in characteristic of the gas concentration sensor.

The impedance measuring circuit produces an impedance signal indicative of the impedance of the sensor element of the gas concentration sensor and corrects the impedance signal so as to eliminate a variation in the impedance signal caused by the unit-to-unit variation in characteristic of the gas concentration sensor.

The heater control circuit connects with the heater through a power supply conductor for supplying the power to the heater. The heater control circuit has a function of minimizing an error component caused by a resistance value of the power supply conductor.

The signal processing circuit, the impedance measuring circuit, and the heater control circuit are formed on a bare chip mounted on a ceramic substrate.

According to another aspect of the invention, there is provided a gas concentration measuring apparatus which comprises: (a) a gas concentration sensor outputting a signal as a function of concentration of a given component of gasses; (b) a signal processing circuit processing the signal outputted from the gas concentration sensor to provide a voltage signal indicative of the concentration of the given component of the gasses; and (c) a connector having disposed therein the signal processing circuit, the connector having a first end coupled to the signal processing circuit and a second end providing electrical connection with an external device to transmit the voltage signal to the external device.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
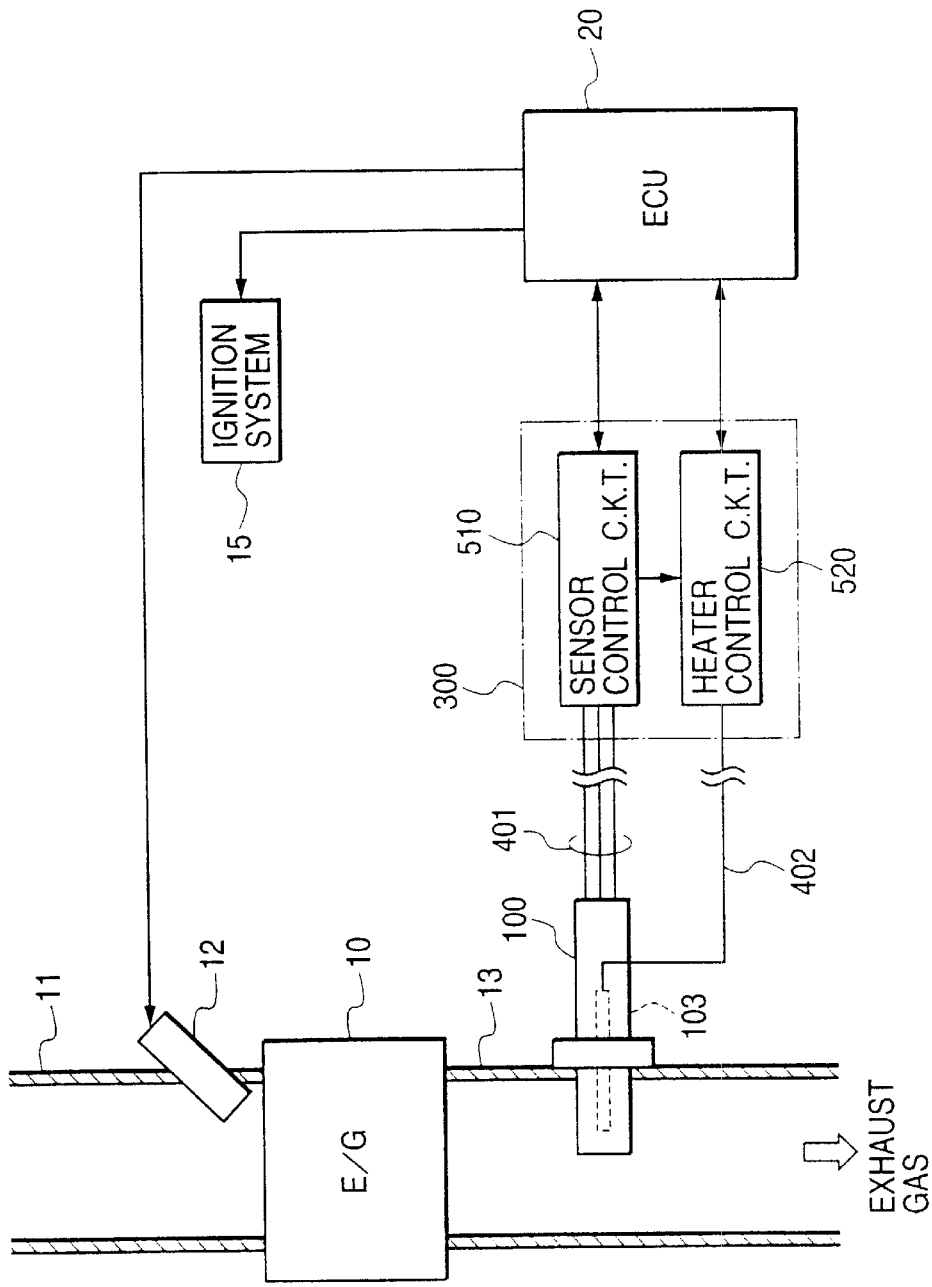
FIG. 1 is a block diagram which shows a gas concentration measuring apparatus according to the invention.

Referring now to the drawings, wherein like numbers refer to like parts in several views, particularly to FIG. 1, there is shown a gas concentration measuring apparatus according to the invention which is used with, as one example, an automotive engine control system designed to control the quantity of fuel injected into an internal combustion engine as a function of an output of the gas concentration measuring apparatus under feedback (F/B) control to bring the air-fuel (A/F) ratio into agreement with a target value and to diagnose the deterioration of a catalytic converter installed in an exhaust pipe of the engine.

The gas concentration measuring apparatus uses a composite gas concentration sensor 100 capable of measuring concentrations of oxygen ($O_2$) and nitrogen oxide (NOx) contained in exhaust gasses of a multi-cylinder four-cycle engine simultaneously.

A fuel injector 12 is installed in an intake pipe 11 to supply the fuel to the engine 10. The gas concentration sensor 100 is installed in an exhaust pipe 13 and outputs sensor signals indicative of the concentration of $O_2$ and NOx.

Figure 3:
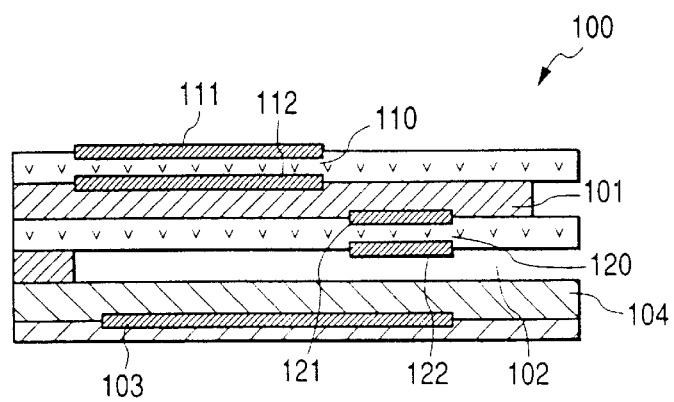
FIG. 3 is a sectional view which shows an internal structure of a gas concentration sensor.

The gas concentration sensor 100 has, as shown in FIG. 3, a two-cell structure designed to measure the concentrations of $O_2$ and NOx contained in exhaust gasses of the engine 10 simultaneously. The gas concentration sensor 100 is made of a lamination of the pump cell 110, the sensor cell 120, a porous diffused layer 101, an air duct 102, an insulating layer 104, and a heater 103. The gas concentration sensor 100 is installed at the right side thereof, as viewed in the drawing, on the exhaust pipe 13 of the engine so as to expose upper, lower, and left surfaces to exhaust gasses.

The pump cell 110 is disposed on the porous diffused layer 101 so that it is exposed to the exhaust gasses. A first pump cell electrode 111 is mounted on the upper surface of the pump cell 110. A second pump cell electrode 112 is mounted on the lower surface of the pump cell 110 facing the porous diffused layer 101. The sensor cell 120 is interposed between the porous diffused layer 101 and the air duct 102. A first sensor cell electrode 121 is attached to an upper surface of the sensor cell 120 facing the porous diffused layer 101. A second sensor cell electrode 122 is attached to a lower surface of the sensor cell 120 facing the air duct 102. The exhaust gasses enters the porous diffused layer 101 from the left side thereof, as viewed in the drawing, and flow in the right direction.

The pump cell 110 and the sensor cell 120 are each formed with a solid electrolyte lamination such as an oxygen ion conductive oxide sintered member made from $ZrO_2$, $HfO_2$, $ThO_2$, and $Bi_2O_3$ in which $CaO$, $MgO$, $Y_2O_3$, and $Yb_2O_3$ are solved as fixing agents. The porous diffused layer 101 is made of a heat-resisting inorganic matter such as alumina, magnesia, silica, spinel, and mullite.

The first pump cell electrode 111 and the first and second sensor cell electrodes 121 and 122 are each made of a noble metal with a high catalytic activity such as platinum (Pt), while the second pump electrode 112 is made of a noble metal such as Au-Pt which is inactive with respect to NOx, that is, hardly decomposes NOx.

The heater 103 is embedded in the insulating layer 104. The insulating layer 104 defines the air duct 102 between itself and the sensor cell 120. The air duct 102 serves as a reference gas chamber into which the air is introduced. The air in the reference gas chamber is used as a reference gas in measuring the concentration of $O_2$. The insulating layer 104 is made of alumina. The heater 103 is made of platinum and cermet such as alumina and supplied with power from a heater control circuit, as will be described later in detail, to produce the heat for activating the whole of the gas concentration sensor 100.

Figure 4A:
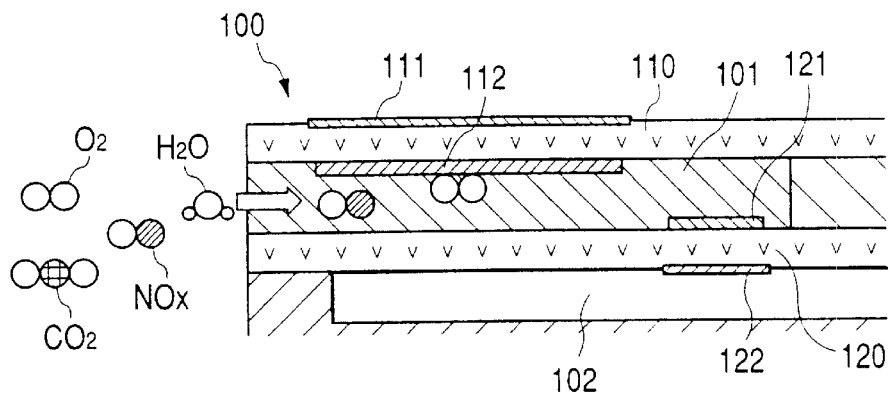
FIGS. 4(a), 4(b), and 4(c) are sectional views which show a sequence of gas measurement operations of a gas concentration sensor.
Figure 4B:
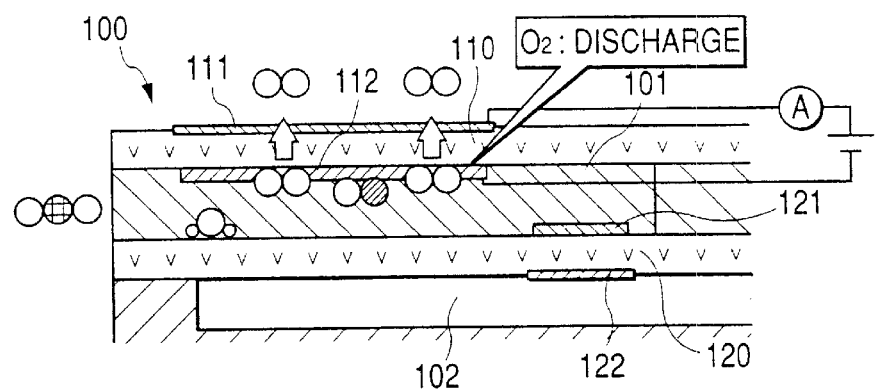
Figure 4C:
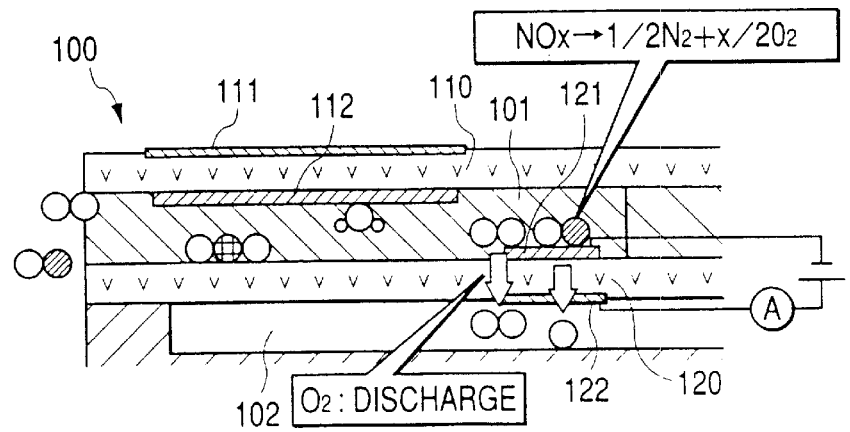

In operation, when exhaust gasses containing $O_2$, NOx, $CO_2$, and $H_2O$, as shown in FIG. 4(a), enter the porous diffused layer 101 and are passing the pump cell 110, application of voltage to the pump cell 110 through the electrodes 111 and 112 causes the exhaust gasses to undergo decomposition. Since the second pump cell electrode 112 is, as described above, made of a noble metal which hardly decomposes NOx, only $O_2$ molecules contained in the exhaust gasses are decomposed or ionized by the pump cell 110, as shown in FIG. 4(*b*), which are, in turn, returned to the exhaust gasses from the first pump cell electrode 111, thereby causing a limiting current (also referred to as a pump cell current below) to flow through the pump cell 110 as a function of the concentration of $O_2$ in the exhaust gasses.

The $O_2$ molecules in the exhaust gasses are usually not decomposed by the pump cell 110 completely, so that residual $O_2$ molecules reach the sensor cell 120. The application of voltage to the sensor cell 120 causes the first sensor cell electrode 121 to decompose the $O_2$ and NOx molecules, as shown in FIG. 4(*c*), so that oxygen ions are discharged to the air duct 102 through the second sensor cell electrode 122, thereby causing a limiting current (also referred to as a sensor cell current or a NOx current below) to flow through the sensor cell 120 as a function of the concentration of NOx.

Figure 5:
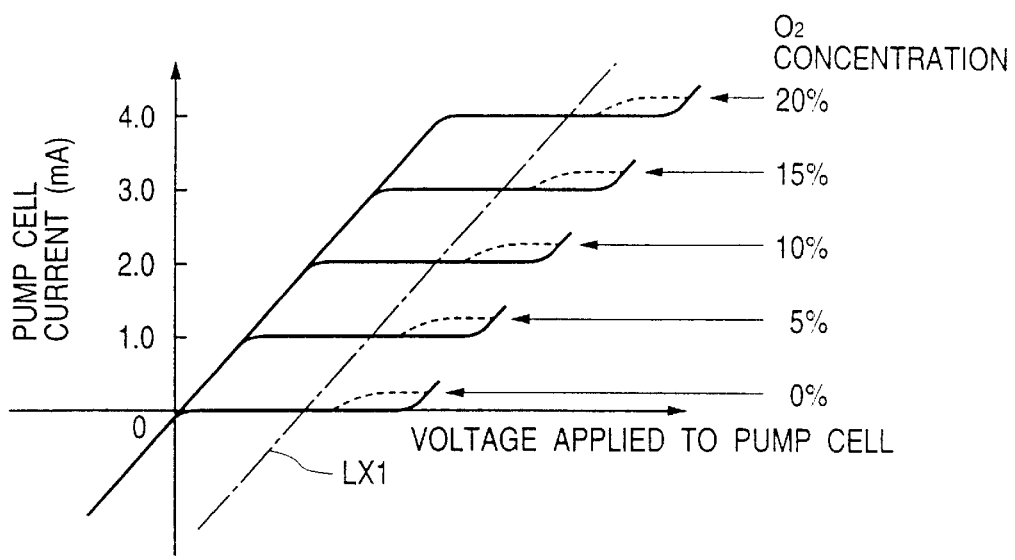
FIG. 5 is a graph which shows a relation between a pump cell current produced by a pump cell and a voltage applied to the pump cell.

FIG. 5 shows a V-I relation between the voltage applied to the pump cell 110 and the pump cell current (mA) outputted from the pump cell 110. Straight segments of lines extending parallel to the abscissa axis indicate limiting current measurable ranges, respectively, which are shifted to the positive side of voltage applied to the pump cell 110 as the concentration of $O_2$ increases. Therefore, if the voltage applied to the pump cell 110 is kept constant when the concentration of $O_2$ is changing, the concentration of $O_2$ may exceed a corresponding one of the limiting current measurable ranges, resulting in difficulty in measuring the concentration of $O_2$ accurately. This also means that a large quantity of $O_2$ reaches the sensor cell 120 without being discharged from the pump cell 110, thereby causing an error component contained in the NOx current to be increased. In order to avoid this, the voltage to be applied to the pump cell 110 is regulated so that it changes at a rate equivalent to a rate of change in dc resistance component of the pump cell 110 as a function of the voltage applied to the pump cell 110. Specifically, the voltage to be applied to the pump cell 110 is changed along a broken line LX1 so that an output of the pump cell 110 may fall within any one of the limiting current measurable ranges at all the time regardless of the concentration of $O_2$ in the exhaust gasses.

Figure 6:
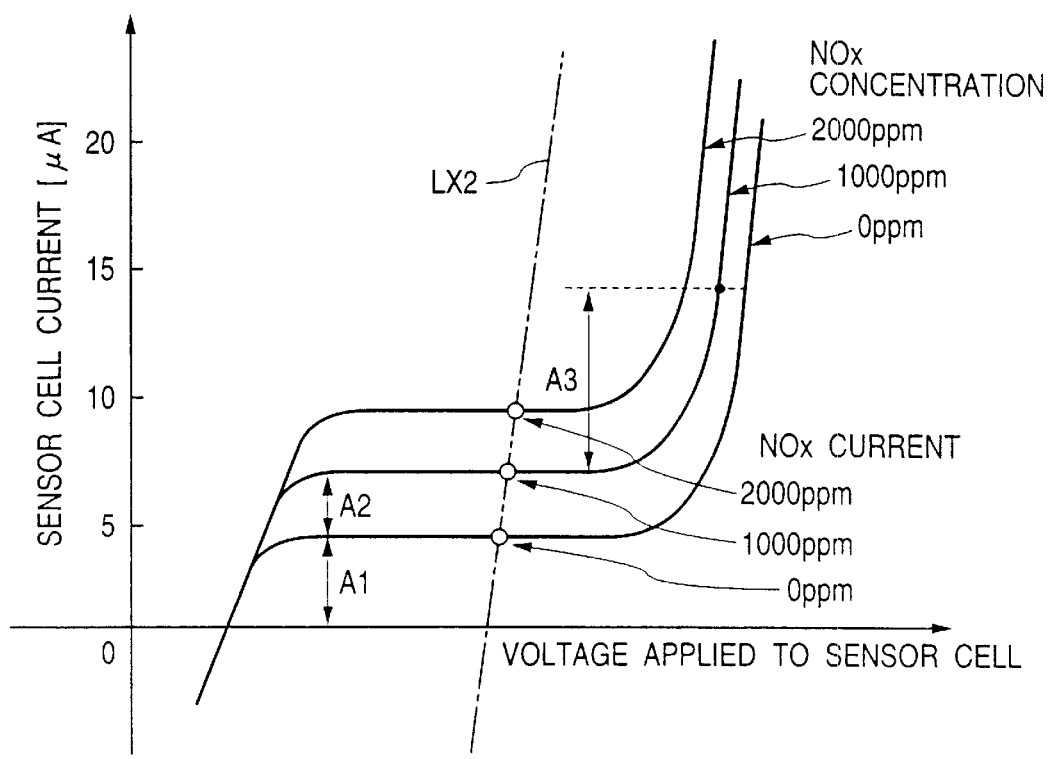
FIG. 6 is a graph which shows a relation between a sensor cell current flowing through a sensor cell and a voltage applied to the sensor cell.

FIG. 6 shows a V-I relation between the voltage applied to the sensor cell 120 and the sensor cell current (mA) outputted from the sensor cell 120. In a range where the concentration of NOx is zero (0) ppm, only a current, as indicated by A1, produced by the residual $O_2$ molecules flowing through the porous diffused layer 101 to the sensor cell 120 is outputted from the sensor cell 120 as the offset current. In a range where the concentration of NOx is greater than zero (0) and smaller than 1,000 ppm, a current, as indicated by A2, produced by the decomposition of NOx by the sensor cell 120 is also outputted from the sensor cell 120. If the voltage applied to the sensor cell 120 exceeds a certain upper limit, it will cause an additional current, as indicated by A3, produced by decomposition of $H_2O$ to be also outputted from the sensor cell 120. Straight segments of lines extending parallel to the abscissa axis indicate limiting current measurable ranges, respectively, where it is possible to measure the NOx decomposition-produced current and which are slightly shifted to the positive side of voltage applied to the sensor cell 120 as the concentration of NOx increases. The voltage applied to the sensor cell 120 is, therefore, controlled along a broken line LX2 so that an output of the sensor cell 120 may fall within one of the limiting current measurable ranges at all the time regardless of the concentration of NOx in the exhaust gasses.

Returning back to FIG. 1, the gas concentration measuring apparatus also includes an electronic control unit (ECU) 20, a sensor control circuit 510, and a heater control circuit 520.

The ECU 20 receives an output of the gas concentration sensor 100 and engine operating data on engine speed, inlet air pressure, water temperature, and throttle opening measured by known sensors (not shown) to control the quantity of fuel supplied by the fuel injector 12 and the ignition timing through an ignition system 15. The ECU 20 also receives an $O_2$ concentration signal which is proportional to an air-fuel ratio of a mixture supplied to the engine 10 and which will also be referred to as an A/F signal and a NOx concentration signal outputted from the sensor control circuit 510.

The sensor control circuit 510 picks up the pump cell current and the sensor cell current from the gas concentration sensor 100 to calculate the concentrations of $O_2$ and NOx in the exhaust gasses and outputs signals indicative thereof to the ECU 20. The sensor control circuit 510 also picks up data on a sensor element temperature determined as a function of a sensor element resistance which indicates the active state of the gas concentration sensor 100 and outputs a signal indicative thereof to the ECU 20.

The heater control circuit 520, as will be described later in detail, receives the sensor element temperature data from the ECU 20 to control the power supply to the heater 103 for maintaining the gas concentration sensor 100 activated.

The sensor control circuit 510 and the heater control circuit 520 are built in a connector 300 connecting between the ECU 20 and the gas concentration sensor 100. Specifically, in a typical prior art structure, the sensor control circuit 510 and the heater control circuit 520 are disposed in the ECU 20, but in this embodiment, they are integrated near the gas concentration sensor 100. This is because there are three main reasons below:

1 The sensor cell current flowing through the sensor cell is in the range of 0 to 2.5 µA, corresponding to a NOx concentration between 0 and 500 ppm. The detection of ±5 ppm requires a measurement accuracy better than ±25 nA. Such low currents are very sensitive to electromagnetic fields and noise if lowing in long wires.

2 For the achievement of a resolution of 2.5 nA, the insulation resistance between wires of a circuit measuring the sensor cell current. This value is much higher than what can be realized within standard automotive wiring harness environment.

3 The exact calibration for the NOx and $O_2$ characteristics (gain and offset) in serial production referring to piece to piece variation can be more easily achieved with a circuit which is nearest to the gas concentration sensor 100.

The oxygen concentration determining circuit 511, the NOx concentration determining circuit 512, the impedance measuring circuit 513, and the heater control circuit 520 may be formed on a single bare chip mounted on a ceramic substrate or a ceramic multi-layered board, thereby also resulting in a compact structure and greatly improved heat and vibration resistances. The sensor control circuit 510 connects electrically with the gas concentration sensor 100 through conductors 401. The heater control circuit 520 connects electrically with the heater 103 through a conductor 402.

Figure 11:
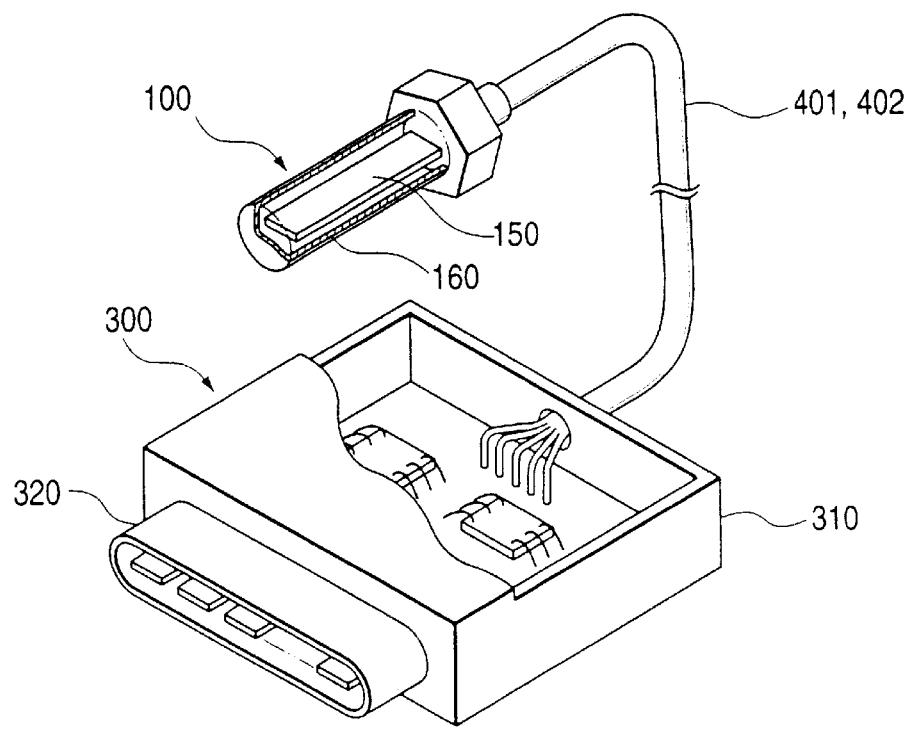
FIG. 11 is a perspective view which shows a gas concentration sensor and a connector in which a sensor control circuit and a heater control circuit are disposed.

The gas concentration sensor 100, as clearly shown in FIG. 11, has a cover 160 and a sensor element 150 disposed within the cover 160. The sensor element 150 consists of the pump cell 110, the sensor cell 120, and the heater 103, as shown in FIG. 3. The cover 160 has formed therein a plurality of pin holes through which the exhaust gasses flow into the cover 160. The connector 300 includes a casing 310 and a plug 320. The casing 310 has disposed therein the sensor control circuit 510 and the heater control circuit 520, thereby minimizing addition of external electric noises thereto.

Figure 2:
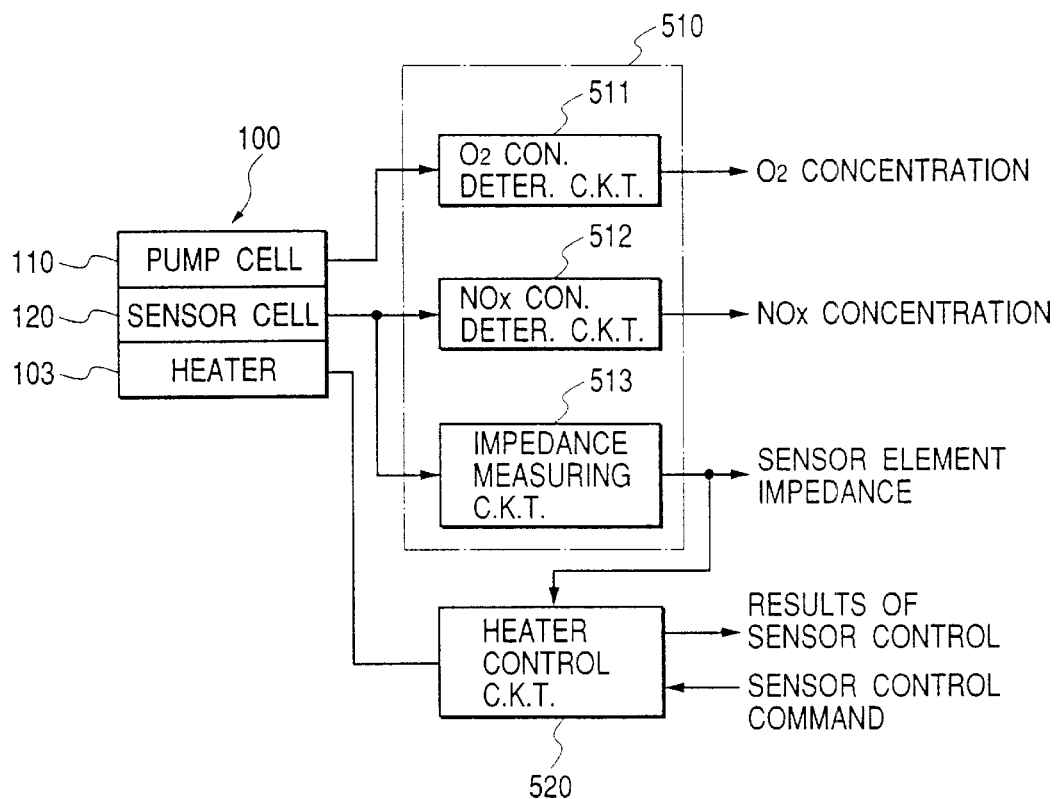
FIG. 2 is an illustration which shows structures of a gas concentration sensor and a sensor control circuit.

The sensor control circuit 510 includes, as clearly shown in FIG. 2, an oxygen concentration determining circuit 511, a NOx concentration determining circuit 512, and a sensor element impedance measuring circuit 513.

The oxygen concentration determining circuit 511 is connected to the pump cell 110 of the gas concentration sensor 100 to measure an electric current or the pump cell current flowing through the pump cell 110 as a function of the concentration of $O_2$ and converts it into a voltage signal which is, in turn, outputted to the ECU 20. The oxygen concentration determining circuit 511 is also responsive to the pump cell current to adjust the voltage applied to the pump cell 110. Similarly, the NOx concentration determining circuit 512 is connected to the sensor cell 120 to measure an electric current or the sensor cell current flowing through the sensor cell 120 as a function of the concentration of NOx and converts it into a voltage signal which is, in turn, outputted to the ECU 20. The $NO_x$ concentration determining circuit 512 is also responsive to the sensor cell current to adjust the voltage applied to the sensor cell 120.

The sensor element impedance measuring circuit 513 measures the impedance of the sensor cell 120 or the pump cell 110 in a sweep method and outputs a signal indicative thereof to the heater control circuit 520.

The heater control circuit 520 is responsive to the signal indicative of the impedance outputted from the sensor cell impedance measuring circuit 513 to control the power supply to the heater 103. Japanese Patent Application No. 10-275521 and Japanese Patent First Publication No. 8-278279 teach heater control systems, disclosure of which is incorporated herein by reference.

Figure 7:
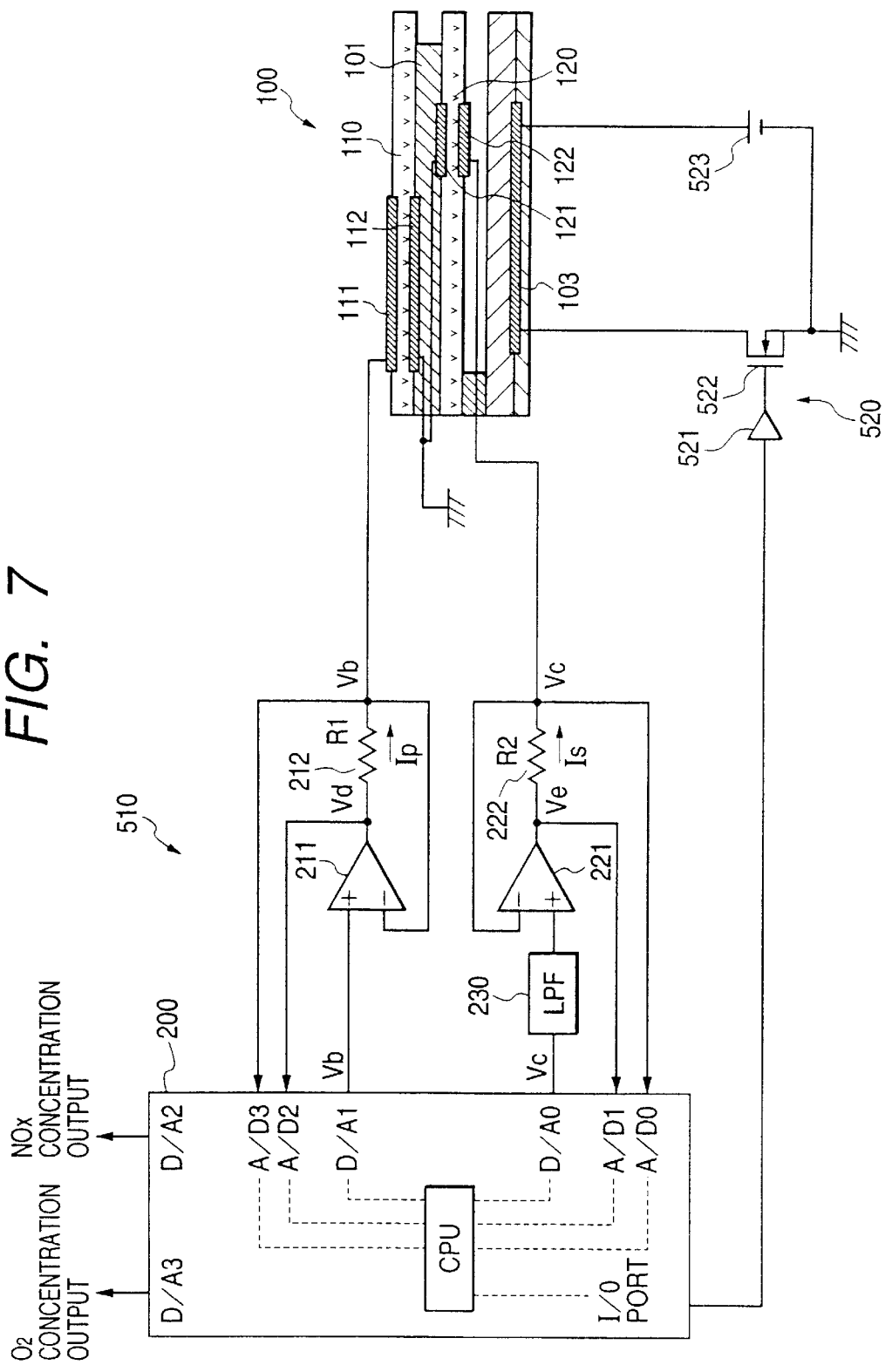
FIG. 7 is a circuit diagram which shows structures of a sensor control circuit and a gas concentration sensor.

The sensor control circuit 510 includes, as clearly shown in FIG. 7, a microcomputer 200 consisting of a CPU, A/D converters, and D/A converters. To the A/D converters A/D0 to A/D3, voltages appearing at terminals Vc, Ve, Vd, and Vb are inputted. From the D/A converters D/A1 and D/A0, a pump cell control voltage Vb and the sensor cell control voltage Vc are outputted. From the D/A converters D/A2 and D/A3, an $O_2$ concentration output and a NOx concentration output are provided.

Specifically, the pump cell control voltage Vb is inputted to an non-inverting input of the amplifier 211. An output of the amplifier 211 is connected to one end of the resistor 212 used in measuring the pump cell current Ip flowing through the pump cell 110 as a function of the concentration of $O_2$. The other end of the resistor 212 is connected to the first pump cell electrode 111 of the gas concentration sensor 100 and an inverting input of the amplifier 211, thereby controlling the voltage appearing at the first pump cell electrode 111 so as to be kept at the same potential as the pump cell control voltage Vb. The resistor 212 also connects at both ends to the A/D converters A/D2 and A/D3.

Therefore, application of the pump cell control voltage Vb to the pump cell 110 from the sensor control circuit 510 will cause the pump cell current Ip to flow through the resistor 212. The pump cell current Ip is given by the following equation:

$$Ip=(Vd-Vb)/R1$$

where Vb and Vd are voltages appearing at the terminals Vb and Vd across the resistor 212, and R1 is a resistance value of the resistor 212.

The microcomputer 200, the amplifier 211, and the resistor 212 constitute the oxygen concentration determining circuit 511.

The sensor cell control voltage Vc outputted from the D/A converter D/A0 is inputted to an non-inverting input of the amplifier 221 through a low-pass filter 230. The low-pass filter 230 may be a primary filter consisting of a capacitor. An output of the amplifier 221 is connected to one end of the resistor 222 used in measuring the sensor cell current Is flowing through the sensor cell 120 as a function of the concentration of NOx. The other end of the resistor 222 is connected to the second sensor cell electrode 122 of the gas concentration sensor 100 and an inverting input of the amplifier 221, thereby controlling the voltage appearing at the second sensor cell electrode 122 to be kept at the same potential as the sensor cell control voltage Vc. The resistor 222 connects at both ends thereof to the A/D converters A/D0 and A/D1 of the microcomputer 200.

Therefore, application of the sensor cell control voltage Vc to the sensor cell 120 from the sensor control circuit 510 will cause the sensor cell current Is to flow through the resistor 222. The sensor cell current Is is given by the following equation:

$$Is=(Ve-Vc)/R2$$

where Ve and Vc are voltages appearing at the terminals Ve and Vc across the resistor 222 and R2 is a resistance value of the resistor 222.

The microcomputer 200, the amplifier 221, and the resistor 222 constitute the NOx concentration determining circuit 512.

The microcomputer 200 measures an a.c. impedance of the sensor cell 120 using the sweep method. Specifically, the measurement of the AC impedance is achieved by changing the sensor cell control voltage Vc outputted from the D/A converter D/A0 instantaneously to apply an ac voltage to the sensor cell 120 which is blurred in the form of a sine wave through the low-pass filter 230. The frequency of the ac voltage is preferably higher than 10 KHz. The time constant of the low-pass filter 230 is in the order of 5 $\mu$s. The microcomputer 200 monitors changes in voltage Ve and Vc appearing at the terminals Ve and Vc through the A/D converters A/D1 and A/D0 to determine a change in voltage difference across the resistor 222 and a change in sensor current and calculates the a.c. impedance of the sensor cell 120 based on the changes in voltage difference and sensor current. The microcomputer 200 outputs a signal indicative of the a.c. impedance of the sensor call 120 to the heater control circuit 520 through a D/A converter or a serial communication port.

The microcomputer 200, the amplifier 221, and the resistor 222 constitute the sensor element impedance measuring circuit 513.

The microcomputer 200 outputs a control signal having a given duty factor through an I/O port to operate a MOSFET driver 521. The MOSFET driver 521 activates the MOSFET 522 to regulate the power supplied from a power source 523 such as a battery to the heater 103 under the PWM control. The microcomputer 200, the MOSFET driver 521, and the MOSFET 522 constitute the heater control circuit 520.

Figure 8:
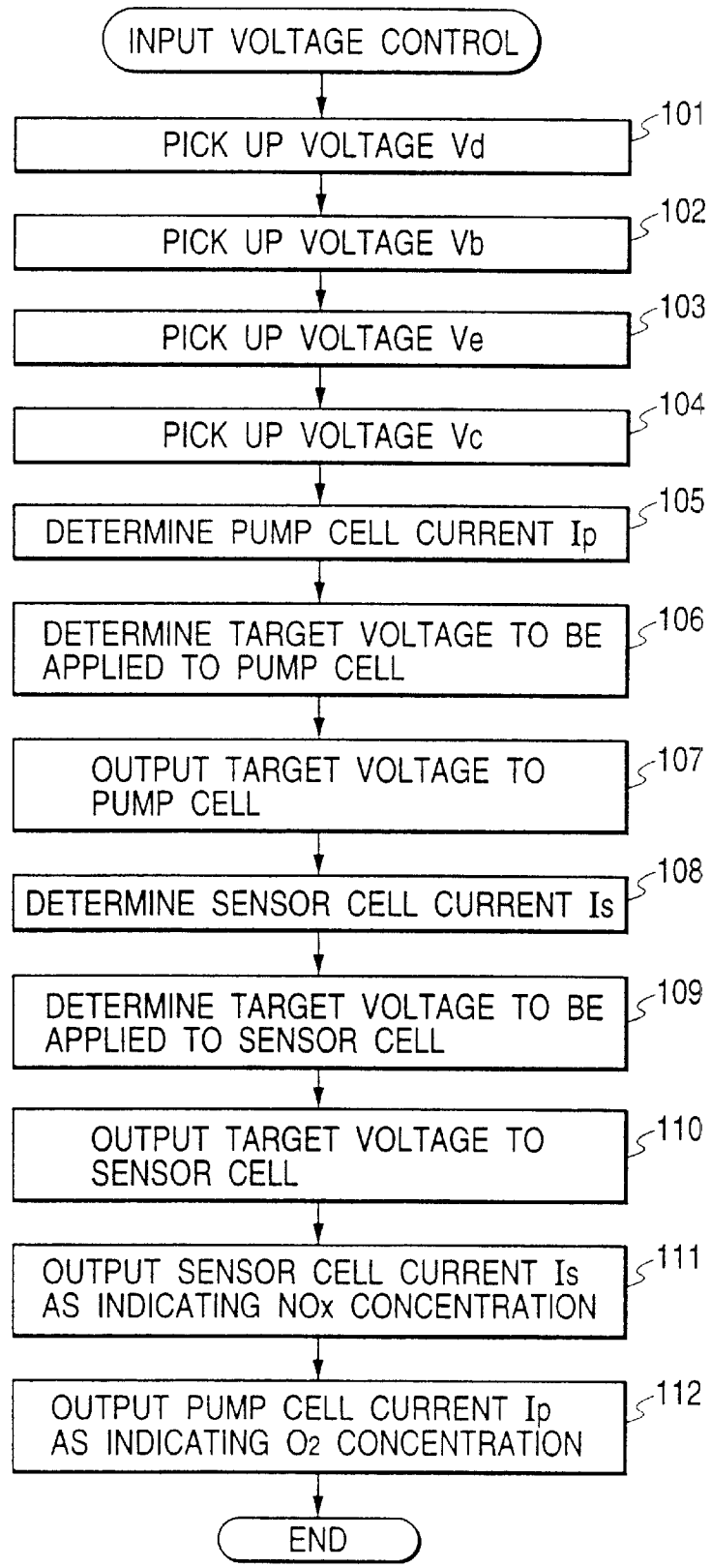
FIG. 8 is a flowchart of a program performed to control voltages applied to a pump cell and a sensor cell of a gas concentration sensor.

FIG. 8 shows a flowchart of a program or a sequence of logical steps performed by the CPU of the microcomputer 200 in the course of execution of a main program (not shown), for example, an air-fuel ratio control program to control the pump cell control voltage Vb and the sensor cell control voltage Vc inputted to the pump cell 110 and the sensor cell 120.

First, in step 101, the CPU picks up the voltage Vd which is developed at the terminal Vd (i.e., one end of the resistor 212) and converted into a digital signal through the A/D converter A/D2. Similarly, in steps 102, 103, and 104, the CPU picks up the voltages Vb, Ve, and Vc which are developed at the terminals Vc, Ve, and Vc and converted into digital signals through the A/D converters A/D3, A/D1, and A/D0, respectively.

After step 104, the routine proceeds to step 105 wherein the pump cell current Ip (=(Vd−Vb)/R1) is determined. The routine proceeds to step 106 wherein a target input voltage to be applied to the pump cell 110 is determined which corresponds to the pump cell current Ip on the voltage line LX1 shown in FIG. 5. The routine proceeds to step 107 wherein the target input voltage determined in step 106 is outputted as the pump cell control voltage Vb through the D/A converter D/A1.

The routine proceeds to step 108 wherein the sensor cell current Is (=(Ve−Vc)/R2) is determined. The routine proceeds to step 109 wherein a target input voltage to be applied to the sensor cell 120 is determined which corresponds to the sensor cell current Is on the voltage line LX2 shown in FIG. 6. The routine proceeds to step 110 wherein the target input voltage determined in step 109 is outputted as the sensor cell control voltage Vc through the D/A converter D/A0.

The routine proceeds to step 111 wherein the sensor cell current Is is outputted as indicating the concentration of NOx to the ECU 20 through, for example, a serial communication port. The routine proceeds to step 112 wherein the pump cell current Ip is outputted as indicating the concentration of $O_2$ to the ECU 20 through, for example, a serial communication port.

Figure 9:
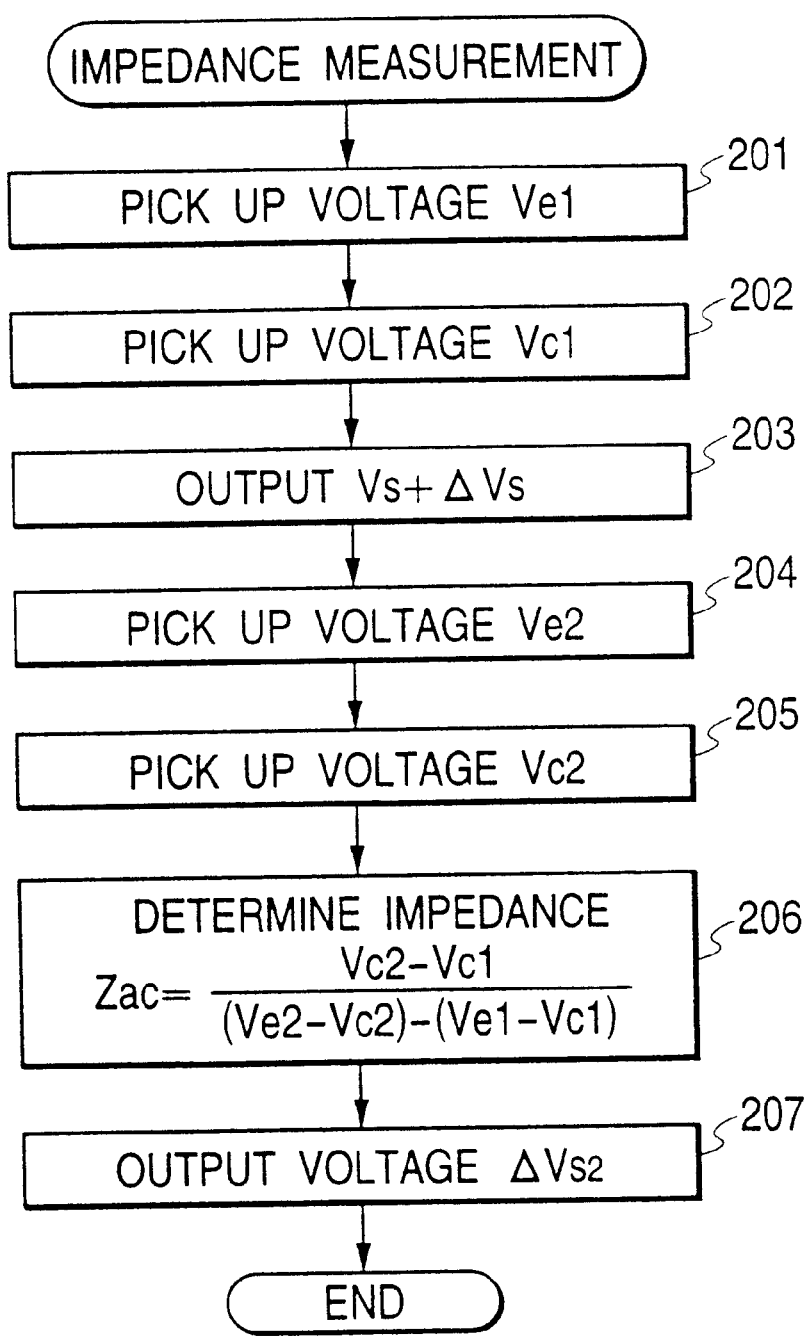
FIG. 9 is a flowchart of a program performed to measure the impedance of a sensor element of a gas concentration sensor.

FIG. 9 shows a subprogram for determining the sensor element impedance which is executed by the CPU of the microcomputer 200 selectively at regular intervals of 128 ms in a start-up mode of engine operation and at regular intervals of 256 ms after the engine is warmed up.

After entering the program, the routine proceeds to steps 201 and 202 wherein the voltages Ve and Vc developed across the resistor 222 are picked up through the A/D converters A/D1 and A/D0, which will be referred to as Ve1 and Ve2 below.

Figure 10:
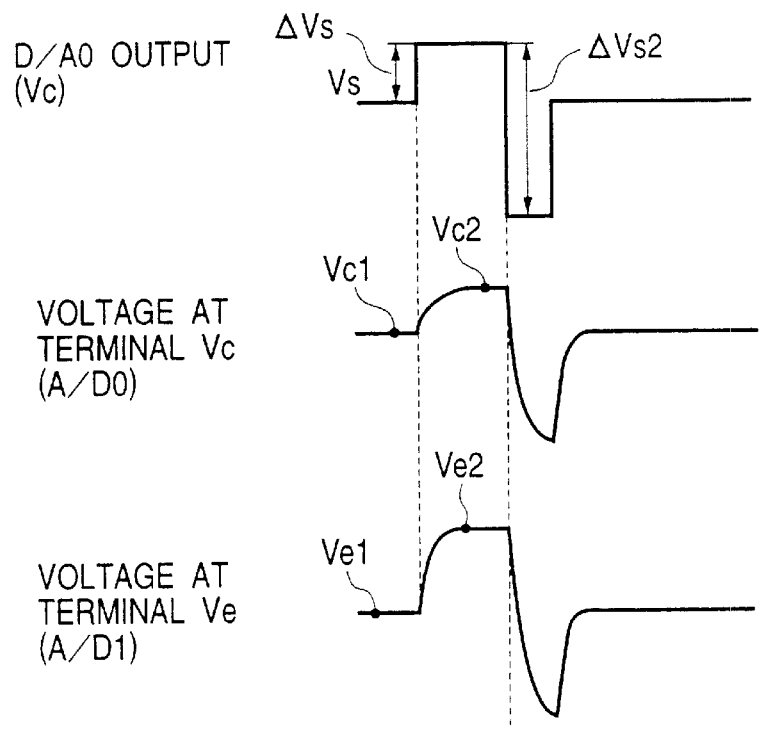
FIG. 10 is a time chart which shows a relation among an output voltage Vs, a terminal voltage Vc, and a terminal voltage Ve.

The routine proceeds to step 203 wherein the sum of a sensor cell control voltage Vs now applied to the sensor cell 120 and an additional a.c. voltage ΔVs is outputted from the D/A converter D/A0, thereby causing, as shown in FIG. 10, the voltages Vc and Ve developed across the resistor 222 to change in the form of a sine wave according to the time constant of the low-pass filter 230.

The routine proceeds to steps 204 and 205 wherein the voltages appearing at the terminals Ve and Vc, which will be referred to as Ve2 and Vc2 below, are picked up 20 μs after the voltage applied to the resistor 222 is changed in step 203.

The routine proceeds to step 206 wherein the impedance Zac of the sensor cell 120 is calculated according to an equation below:

$$Zac=(Vc2-Vc1)/\{(Ve2-Vc2)-(Ve1-Vc1)\}$$

The routine proceeds to step 207 wherein a negative voltage Δ Vs2 is, as shown in FIG. 10, outputted from the D/A converter D/A0 temporarily to return the voltage applied to the sensor cell 120 to the voltage Vs.

Figure 12:
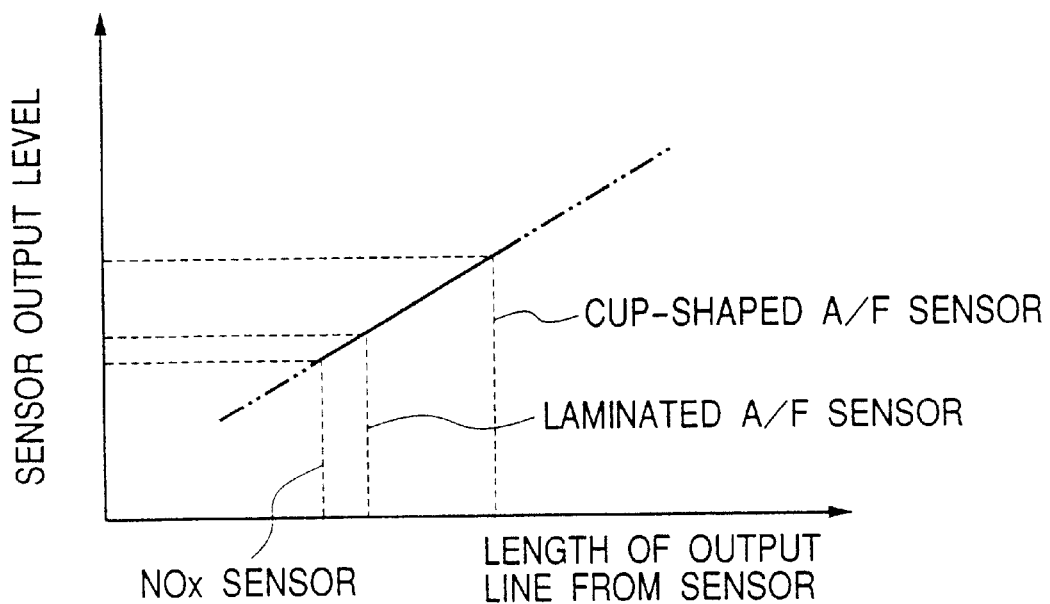
FIG. 12 is a graph which shows a relation of levels of signal outputs from a cup-shaped A/F sensor, a laminated A/F sensor, and a NOx sensor to the length of an output line extending from each of the sensors.

An electric current flowing through the gas concentration sensor 100 as a function of the concentration of each of $O_2$ and NOx is, as described above, extremely weak, so that it apt to interfere with electrical noises produced from peripheral devices. Particularly, when the concentration of NOx is within 0 to 2000 ppm, the current outputted from the gas concentration sensor 100 as a function of the concentration of NOx is, as shown in FIG. 6, as little as 5 to 10 μA, thus resulting in a failure in measuring the concentration of NOx accurately. In order to avoid this problem, this embodiment specifies the length of the conductors 401 connecting between the gas concentration sensor 100 and the sensor control circuit 510 and the length of the conductor 402 connecting between the heater 103 and the heater control circuit 520 using a suitable relation, as shown in FIG. 12, between the length of a wire extending from each of a cup-shaped A/F sensor, a laminated A/F sensor, and a NOx sensor (i.e., the gas concentration sensor 100) and the level of an output signal thereof.

Generally, a gas concentration sensor such as the one in this embodiment designed to measure the concentration of NOx is required to shorten the length of wire extending therefrom as compared with the cup-shaped or laminated A/F sensors. Minimizing the interference of an output of the gas concentration sensor 100 with electric noises, thus, requires decreasing the length of the conductors 401 and 402. Further, in a case where the gas concentration sensor 100 is mounted in an automotive vehicle, various electric noises are added to an output of the gas concentration sensor 100. Therefore, the lower the level of the output of the gas concentration sensor 100, the better the decrease in distance between the gas concentration sensor 100 and the connector 300 to minimize the electric noises.

Figure 13:
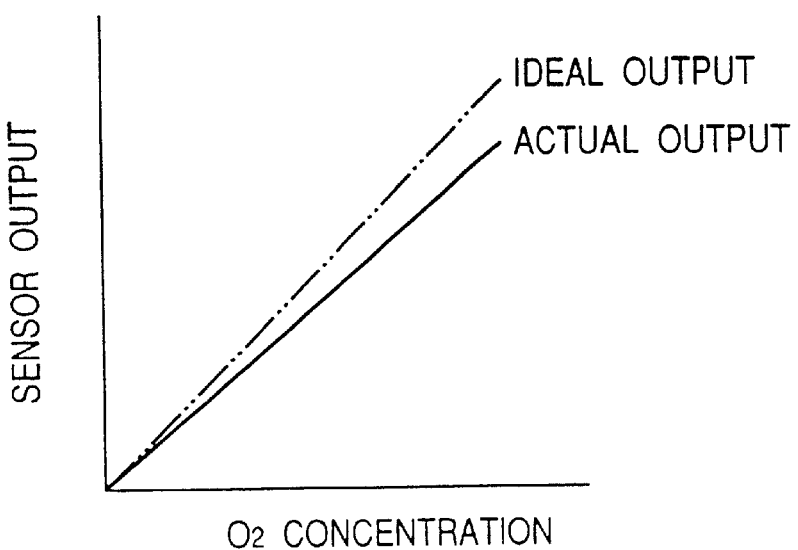
FIG. 13 is a graph which shows a relation between an actual output of a gas concentration sensor and a correct one.

The sensor element of the gas concentration sensor 100 contains ceramic, so that it has characteristics of a flow of d.c. current, and a flow of a.c. current, and an output indicating the concentration of gas that undergo an inevitable unit-to-unit deviation in mass production, thus resulting in a decrease in production yield. Specifically, a small variation in production condition will cause the characteristics and the impedance of sensors to change. Some of the sensors whose characteristics are below standards are usually discarded, thus resulting in a decrease in production yield. For example, when the concentration of $O_2$ varies, as shown in FIG. 13, an actual output of the gas concentration sensor 100, as indicated by a solid line, is shifted from a correct one, as indicated by a broken line.

Additionally, the resistance value of the heater 103 is set small in order to speed up the activity of the gas concentration sensor 100. At the start of the control of the heater 103, it is usually difficult to measure the impedance of the gas concentration sensor 100 sensor accurately. The ECU 20 may, thus, monitor the power supplied to the heater 103 from the heater control circuit 520 (i.e., the heater voltage and current) and provide a power supply control signal to the heater control circuit 520. If, therefore, the resistance value of the conductor 402 (including resistance values of the heater 103 and the heater control circuit 520) differs among vehicles, it will cause the controllability of the heater 103 to vary, resulting in, for example, a decrease in heat produced by the heater 103 and an error in measuring the power supplied to the heater 103, which may lead to a delay in activating the gas concentration sensor 100 and overheating thereof.

In order to avoid the above problems, the sensor control circuit 510 of this embodiment is, as described later in detail, designed to adjust or correct the characteristics of the gas concentration sensor 100, and the heater control circuit 520 is designed to compensate for the error in measuring the power supplied to the heater 103 depending upon the resistance of the conductor 402.

Specifically, the correction of the characteristics of the gas concentration sensor 100 and the compensation of the error in measuring the power supplied to the heater 103 are accomplished with gain adjustment and offset adjustment in the sensor control circuit 510 and the heater control circuit 520 in manufacturing processes. Such adjustments may be achieved with 1 installation of adjustment parts,
2 installation and trimming of a thick-film resistor, or
3 trimming a resistor on an IC chip in which the sensor control circuit 510 and the heater control circuit 520 are integrated.

Figure 14:
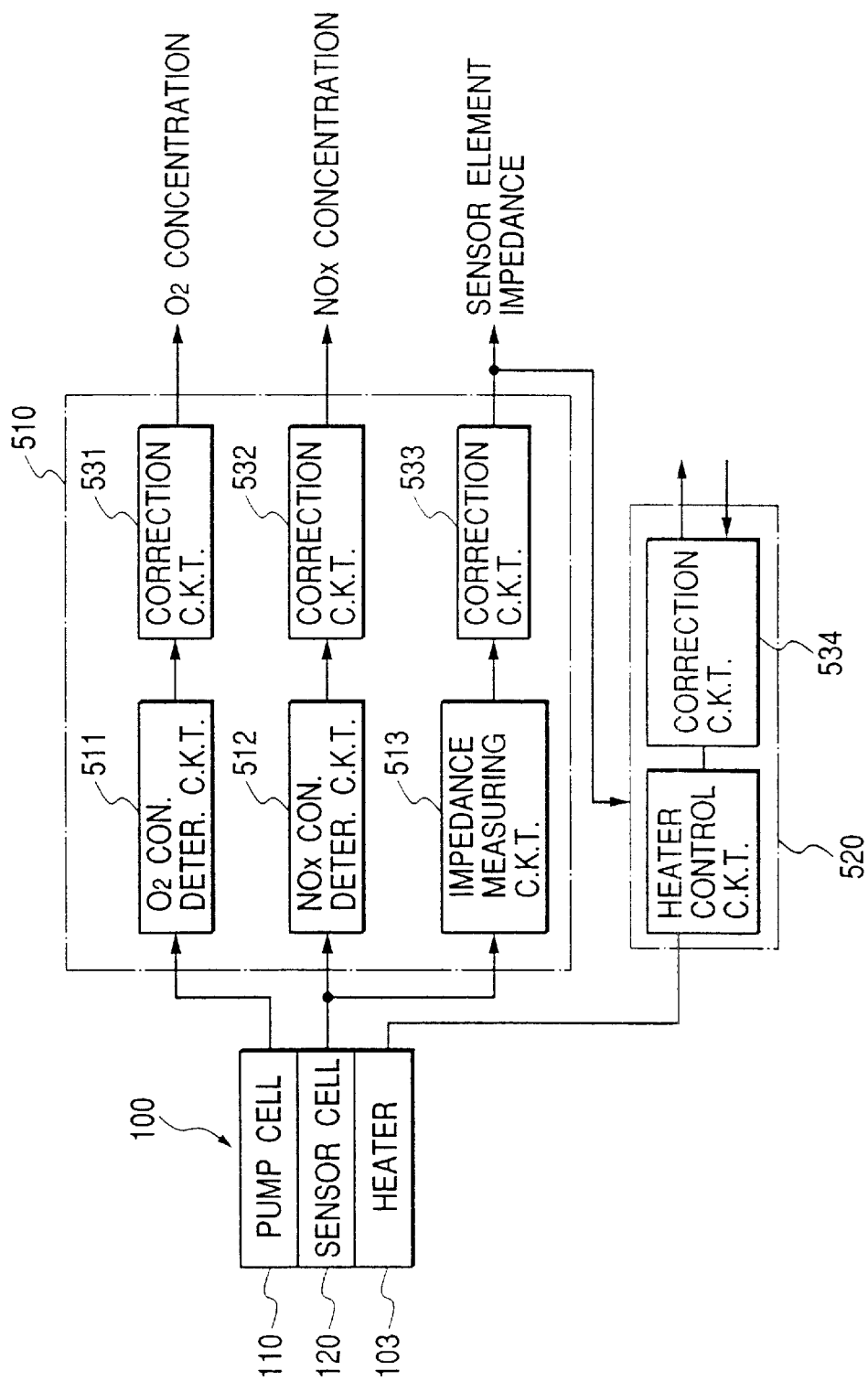
FIG. 14 is a block diagram which shows a gas concentration measuring apparatus in which output correction circuits are disposed.

As one example, correction circuit 531, 532, and 533, as shown in FIG. 14, may be connected to outputs of the oxygen concentration determining circuit 512, the NOx concentration determining circuit 512, and the impedance measuring circuit 513, respectively. Each of the correction circuits 531, 532, and 533 is made of a resistor such as a shunt which is trimmed to adjust a resistance value thereof so as to bring an actual output of a corresponding one of the oxygen concentration determining circuit 511, the NOx concentration determining circuit 512, and the impedance measuring circuit 533 into agreement with a correct or desired one.

Alternatively, a gain/offset adjustment map may be pre-stored in the microcomputer 200 which is used in calculating and adjusting a gain or an offset of the amplifiers 211 and 221 to bring an actual output of each of the oxygen concentration determining circuit 512, the NOx concentration determining circuit 512, and the impedance measuring circuit 533 into agreement with a correct or desired one. Instead of use of the gain/offset adjustment map, parameters used in calculating and adjusting the gain and offset may be inputted directly to the microcomputer 200 through an A/D converter.

In order to eliminate an error component contained in an output signal of the heater control circuit 520 indicating the amount of power supplied to the heater 103 due to the resistance of the conductor 402, a correction circuit 534, similar to one of the correction circuits 531, 532, and 533, may be built in the heater control circuit 520. Alternatively, the microcomputer 200 may calculate a gain or an offset of the heater control circuit 520 in the same manner as described above to bring the output signal into agreement with a correct one.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments which can be embodied without departing from the principle of the invention as set forth in the appended claims.

For example, only the NOx concentration determining circuit 512 which receives a weak electrical signal (i.e., the sensor cell current) from the gas concentration sensor 100 may be disposed within the connector 300 to shorten the distance to the gas concentration sensor 100 or the length of a conductor connecting between the NOx concentration determining circuit 512 and the gas concentration sensor 100 for minimizing addition of electrical noises. Additionally, any one of the oxygen concentration determining circuit 511, the impedance measuring circuit 513, and the heater control circuit 520 may also be disposed within the connector 300, thereby allowing the length of conductors between the circuits 511, 512, 513, and 520 and the gas concentration sensor 100 to be determined selectively, thus resulting in an increase in freedom of design.

The first sensor cell electrode 121 and the second pump cell electrode 112 are, as clearly shown in FIG. 7, connected to ground, but may alternatively be connected to a common terminal which is kept at a positive potential. This allows a negative electric current to flow through each of the pump cell 110 and the sensor cell 120. Thus, even when a rich gas which usually reduces a flow of the negative current and changes a balance of concentration of $O_2$ in the porous diffused layer 101 enters the gas concentration sensor 100, it becomes possible to keep the concentration of gas, for example, $O_2$ in the porous diffused layer 101 at a constant value equivalent to the stoichiometric. This enables the rich gas to be measured accurately, thus resulting in an increase in measurable range of the gas concentration sensor 100 and also results in greatly improved response rate of the gas concentration sensor 100 when the gas returns from the rich to lean side.

The present invention may be used with an air-fuel ratio (A/F) sensor designed to measure the concentration of $O_2$ contained in exhaust gasses of an internal combustion engine for determining an air-fuel ratio of a mixture supplied to the engine. As such an A/F sensor, a cup-shaped A/F sensor in which a solid electrolyte body and a diffused resistance layer are cup-shaped and a laminated A/F sensor made of a lamination of a solid electrolyte plate and a diffused resistance layer are known. When the air-fuel ratio is 12 to 18, the laminated A/F sensor outputs a current signal of as little as −0.75 to 0.4 mA, but the structure of this invention reduces addition of electric noises to an output of the laminated A/F sensor sufficiently.

The present invention may also be used with three-cell or four-cell gas concentration sensors which are known in the art.

The present invention may further be used with a gas concentration sensor which is designed to decompose and discharge $O_2$ contained in gasses to be measured through a pump cell and decompose HC and/or CO contained in the gasses after the decomposition of $O_2$ through a sensor cell for determining the concentration of $O_2$ and the concentration of HC and/or CO.

What is claimed is:

1. A gas concentration measuring apparatus comprising:
   a gas concentration sensor having a sensor element and an electrical connector for connection to a remote digital signal processor,
   said sensor element including a pump cell and a sensor cell, the pump cell being made of a solid electrolyte body and a first and a second pump cell electrode, the first and second pump cell electrodes being responsive to application of voltage to disassociate and pump oxygen molecules contained in exhaust gases of an automotive engine to which said gas concentration sensor is exposed out of said gas concentration sensor, said sensor cell being made of a solid electrolyte body and a first and a second sensor cell electrode, the first and second sensor cell electrodes being responsive to application of voltage to disassociate at least one of $NO_x$, HC, and CO contained in the exhaust gases through the first sensor cell electrode to produce a current signal flowing through the solid electrolyte body as a function of concentration of the at least one of $NO_x$, HC, and CO; and
   a microcomputer disposed within said connector performing functions of a gas concentration determining, impedance measuring, and heater control, the gas concentration determining being functionally connected to the first and second sensor cell electrodes to process and analyze the current signal provided by said gas concentration sensor to output data as a function of the concentration of the at least one of $HO_x$, HC, and CO to said remote digital signal processor through serial digital signal communication, the impedance measuring function measuring an impedance of the sensor element of said gas concentration sensor, the heater control function controlling power supply to a heater which heats the sensor element based on the measured impedance.

2. A gas concentration measuring apparatus as in claim 1 wherein said microcomputer measures a current flowing through the first and second pump cell electrodes of said pump cell and determines a target voltage to be applied to the first and second pump cell electrodes as a function of the measured current.

3. A gas concentration measuring apparatus as in claim 1 wherein said gas concentration sensor has an expected minimum level of output current during normal sensing operation and further comprising:

a conductor electrically connecting said gas concentration sensor and said microcomputer for transmission of the current signal from said gas concentration sensor to said microcomputer, said conductor having a length selected as a function of said expected minimum level of the current signal outputted from said gas concentration sensor.

4. A method for operating a gas concentration sensor having a sensor element and an electrical connector for connection to a remote digital signal processor, said sensor element including a pump cell and a sensor cell, the pump cell being made of a solid electrolyte body and a first and a second pump cell electrode, the first and second pump cell electrodes being responsive to application of voltage to disassociate and pump oxygen molecules contained in exhaust gases of an automotive engine to which said gas concentration sensor is exposed out of said gas concentration sensor, said sensor cell being made of a solid electrolyte body and a first and a second sensor cell electrode, the first and second sensor cell electrodes being responsive to application of voltage to disassociate at least one of $NO_x$, HC, and CO contained in the exhaust gases through the first sensor cell electrode to produce a current signal flowing through the solid electrolyte body as a function of concentration of the at least one of $NO_x$, HC, and CO, said method comprising:

providing in said connector a microcomputer performing functions of gas concentration determining, impedance measuring, and heater control, the gas concentration determining being functionally connected to the first and second sensor cell electrodes to process and analyze the current signal provided by said gas concentration sensor to output data as a function of the concentration of the at least one of $HO_x$, HC, and CO to said remote digital signal processor through serial digital signal communication, the impedance measuring function measuring an impedance of the sensor element of said gas concentration sensor, the heater control function controlling a power supply to a heater which heats the sensor element based on the measured impedance.

5. A method as in claim 4 wherein said microcomputer measures a current flowing through the first and second pump cell electrodes of said pump cell and determines a target voltage to be applied to the first and second pump cell electrodes as a function of the measured current.

6. A method as in claim 4 wherein said gas concentration sensor has an expected minimum level of output current during normal sensing operation and wherein a gas concentration measuring apparatus as a conductor electrically connects said gas concentration sensor and said microcomputer for transmission of the current signal from said gas concentration sensor to said microcomputer, said conductor having a length selected as a function of said expected minimum level of the current signal outputted from said gas concentration sensor.

* * * * *

(12) EX PARTE REEXAMINATION CERTIFICATE (7793rd)
United States Patent
Hada et al.

(10) Number: US 6,547,955 C1
(45) Certificate Issued: Oct. 5, 2010

(54) GAS CONCENTRATION MEASURING APPARATUS DESIGNED TO MINIMIZE ERROR COMPONENT CONTAINED IN OUTPUT

(75) Inventors: Satoshi Hada, Kariya (JP); Eiichi Kurokawa, Okazaki (JP); Tomoo Kawase, Nagoya (JP); Toshiyuki Suzuki, Handa (JP); Satoshi Haseda, Okazaki (JP)

(73) Assignee: Denso Corporation, Kariya, Aichi-Pref. (JP)

Reexamination Request:
No. 90/010,102, Feb. 7, 2008

Reexamination Certificate for:
Patent No.: 6,547,955
Issued: Apr. 15, 2003
Appl. No.: 09/453,518
Filed: Dec. 3, 1999

(30) Foreign Application Priority Data

Dec. 4, 1998 (JP) ............................................. 10345654

(51) Int. Cl.
G01N 27/41 (2006.01)
G01N 27/00 (2006.01)
G01N 27/26 (2006.01)
G01N 27/407 (2006.01)
G01N 27/416 (2006.01)
G01N 27/419 (2006.01)

(52) U.S. Cl. .......................... 205/781; 204/406; 204/424; 204/425; 205/784.5; 205/785; 205/787

(58) Field of Classification Search ........................ None
See application file for complete search history.

(56) References Cited

U.S. PATENT DOCUMENTS

| 4,214,472 A | 7/1980 | Maxwell et al. |
| 4,337,745 A | 7/1982 | Pomerantz |
| 4,428,348 A | 1/1984 | Takase et al. |
| 4,668,873 A | 5/1987 | Ohba et al. |
| 4,963,246 A | 10/1990 | Nakajima et al. |
| 4,963,249 A | 10/1990 | Baird, Jr. et al. |
| 5,323,635 A | 6/1994 | Ueno et al. |
| 5,812,880 A | 9/1998 | Goto et al. |
| 5,869,744 A | 2/1999 | Suzuki et al. |
| 6,149,786 A | 11/2000 | Patrick et al. |
| 6,254,750 B1 | 7/2001 | Patrick et al. |
| 6,635,161 B2 | 10/2003 | Inagaki |
| 7,050,902 B1 | 5/2006 | Bolz |

FOREIGN PATENT DOCUMENTS

| DE | 89 10 740.3 | 12/1989 |
| DE | 198 36 127 | 2/2000 |
| EP | 0 120 423 A1 | 10/1984 |

(Continued)

OTHER PUBLICATIONS

Kato et al., "Thick Film ZrO2 Nox Sensor", publication 960334, 1996 Society of Automotive Engineers, Inc.

Inagaki et al., "NOx Meter Utilizing ZrO2 Pumping Cell", Publication 980266, 1998 Society of Automotive Engineers, Inc.

(Continued)

*Primary Examiner*—Alan Diamond

(57) ABSTRACT

A gas concentration measuring apparatus which has a gas sensor designed to measure, for example, the concentrations of $O_2$ and HOx contained in exhaust emissions of an automotive engine is provided. The apparatus includes a signal processing circuit which converts a current signal outputted from the gas sensor as a function of the concentration of either of $O_2$ and HOx into a voltage signal. The gas sensor and the signal processing circuit are connected electrically through a conductor. The conductor has a length which is determined as a function of a level of the current signal outputted from the gas sensor. The weaker the level of the current signal is, the shorter the length of the conductor. This minimizes addition of electrical noises to the current signal outputted from the gas sensor.

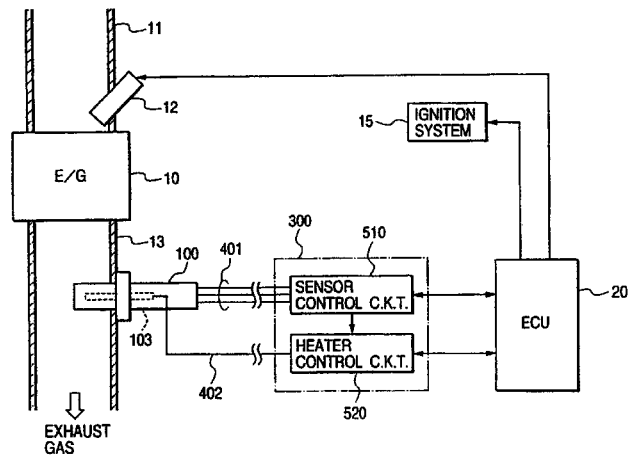

FOREIGN PATENT DOCUMENTS

| | | |
|---|---|---|
| EP | 0 734 905 A2 | 10/1996 |
| EP | 791827 A1 * | 8/1997 |
| EP | 0 841 562 A2 | 5/1998 |
| EP | 0 897 112 | 2/1999 |
| EP | 0 937 979 | 8/1999 |
| JP | 59-128947 | 7/1984 |
| JP | 01-186699 | 7/1989 |
| JP | 03-123850 | 5/1991 |
| JP | 06-050934 | 2/1994 |
| JP | 06-174678 | 6/1994 |
| JP | 8-79841 | 3/1996 |
| JP | 08-249021 | 9/1996 |
| JP | 09-274003 | 10/1997 |
| JP | 09-318594 | 12/1997 |
| JP | 10-111269 | 4/1998 |
| JP | 10-142194 | 5/1998 |
| JP | 10-221298 | 8/1998 |
| JP | 10-300716 | 11/1998 |
| JP | 11-304758 | 11/1999 |
| JP | 2000-171435 | 6/2000 |
| JP | 2007-292490 | 11/2007 |
| WO | WO 98/13686 | 4/1998 |
| WO | WO 99/42717 | 8/1999 |
| WO | WO 00/10002 | 2/2000 |

OTHER PUBLICATIONS

Horowitz, Hill: "Art of Electronics", 1989, p. 673, 674 and 975.

Kato et al., "Performance of Thick Film NOx Sensor on Diesel and Gasoline Engines", Publication 970858, 1997 Societ of Automotive Engineers, Inc.

Kimio Tazaki, "Basic Knowledge of Communications," Nippon Jitsugyo Publishing, pp. 210–212 with partial English translation, 1991.

Dictionary of Science & Technology, The Nikkan Kogyo Shimbun, Ltd., p. 609, Mar. 28, 1996. (extract re sequencer, sequence controller, sequential control).

"Wikipedia," the Free Encyclopedia (extract re sequential control) Jun. 20, 2008.

"Wikipedia," the Free Encyclopedia (extract re programmable logic controller) Jun. 20, 2008.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 3, 4 and 6 are cancelled.
Claims 2 and 5 were not reexamined.

* * * * *